(12) United States Patent
Roomi

(10) Patent No.: US 11,376,030 B2
(45) Date of Patent: Jul. 5, 2022

(54) DEVICES AND METHODS FACILITATING THE MANUFACTURE OF SURGICAL INSTRUMENTS

(71) Applicant: Covidien LP, Mansfield, MA (US)

(72) Inventor: Amir Roomi, Boulder, CO (US)

(73) Assignee: Covidien LP, Mansfield, MA (US)

( * ) Notice: Subject to any disclaimer, the term of this patent is extended or adjusted under 35 U.S.C. 154(b) by 345 days.

(21) Appl. No.: 16/785,781

(22) Filed: Feb. 10, 2020

(65) Prior Publication Data

US 2021/0244426 A1  Aug. 12, 2021

(51) Int. Cl.
| | | |
|---|---|---|
| *A61B 17/29* | (2006.01) | |
| *A61B 17/00* | (2006.01) | |
| *A61B 18/14* | (2006.01) | |

(52) U.S. Cl.
CPC .......... *A61B 17/29* (2013.01); *A61B 18/1445* (2013.01); *A61B 2017/00526* (2013.01); *A61B 2017/2936* (2013.01)

(58) Field of Classification Search
CPC .... A61B 2017/2936; A61B 2017/2947; A61B 2017/00526; A61B 17/29; A61B 17/3468; A61B 18/1445
See application file for complete search history.

(56) References Cited

U.S. PATENT DOCUMENTS

| | | |
|---|---|---|
| 2,619,965 A | 12/1952 | Goldstone |
| 2,704,399 A | 3/1955 | Melcher |
| 3,302,648 A | 2/1967 | Nelson |
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |

(Continued)

FOREIGN PATENT DOCUMENTS

| | | |
|---|---|---|
| CN | 201299462 Y | 9/2009 |
| DE | 2415263 A1 | 10/1975 |

(Continued)

*Primary Examiner* — Majid Jamialahmadi
(74) *Attorney, Agent, or Firm* — Carter, DeLuca & Farrell LLP

(57) ABSTRACT

An insertion tool facilitating assembly of a surgical instrument includes a housing defining a distal end portion, a proximal end portion, and a central lumen. The central lumen extends therethrough the housing between a distal opening and a proximal opening, and defines a proximal portion and a distal portion. The central lumen is configured to receive a portion of a pin within the distal portion thereof. The insertion tool further includes retention channel defined about the housing at the distal end portion thereof. The retention channel is in communication with the central lumen. A D-ring is at least partially seated within the retention channel and extends into the distal portion of the central lumen to retain the pin therein by applying a compressive force to the pin. A plunger is configured to slide through the central lumen to deploy the pin distally from the distal opening of the central lumen.

13 Claims, 11 Drawing Sheets

(56) References Cited

U.S. PATENT DOCUMENTS

| | | |
|---|---|---|
| D354,564 S | 1/1995 | Medema |
| 5,395,375 A | 3/1995 | Turkel et al. |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| 5,951,549 A | 9/1999 | Richardson et al. |
| D416,089 S | 11/1999 | Barton et al. |
| 5,976,132 A | 11/1999 | Morris |
| 6,021,694 A | 2/2000 | Beger |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| 6,322,561 B1 | 11/2001 | Eggers et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| 7,318,725 B2 | 1/2008 | Zepf |
| D564,662 S | 3/2008 | Moses et al. |
| D567,943 S | 4/2008 | Moses et al. |
| 7,393,348 B2 | 7/2008 | Dworschak et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,780,662 B2 | 8/2010 | Bahney |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 8,591,511 B2 | 11/2013 | Romero |
| 2006/0264922 A1 | 11/2006 | Sartor et al. |
| 2007/0249992 A1* | 10/2007 | Bardy ............ A61M 37/0069 604/60 |
| 2016/0345993 A1* | 12/2016 | Fry ................ A61B 18/1445 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | H0540112 A | 2/1993 |
| JP | 6121797 A | 5/1994 |
| JP | 6285078 A | 10/1994 |
| JP | 6511401 | 12/1994 |
| JP | H06343644 A | 12/1994 |
| JP | H07265328 A | 10/1995 |
| JP | 08056955 | 3/1996 |
| JP | 08252263 A | 10/1996 |
| JP | 8289895 A | 11/1996 |
| JP | 8317934 A | 12/1996 |
| JP | 8317936 A | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| SU | 401367 A1 | 11/1974 |
| WO | 0036986 A1 | 6/2000 |
| WO | 0059392 A1 | 10/2000 |
| WO | 0115614 A1 | 3/2001 |

(56) References Cited

FOREIGN PATENT DOCUMENTS

| | | |
|---|---|---|
| WO | 0154604 A1 | 8/2001 |
| WO | 0245589 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

* cited by examiner

DEVICES AND METHODS FACILITATING THE MANUFACTURE OF SURGICAL INSTRUMENTS

FIELD

The present disclosure relates to surgical instruments and, more specifically, to devices and methods facilitating the manufacture of surgical instruments.

BACKGROUND

Various different types of surgical instruments employ pins such as pivot pins, cam pins, retention pins, etc. A surgical forceps, for example, is a pliers-like device which relies on mechanical action between a pair of jaws to grasp, clamp, and constrict tissue. Energy-based surgical forceps utilize both mechanical clamping action and energy to treat, e.g., coagulate, cauterize, and/or seal tissue. Many surgical forceps employ pivot pins and/or cam pins to enable the appropriate movement of the jaws to sufficiently grasp tissue for treating and/or cutting the tissue.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

This disclosure generally relates to devices and methods facilitating the manufacture of surgical instruments.

In aspects, the present disclosure provides an insertion tool facilitating assembly of a surgical instrument. The insertion tool includes a housing having a distal end portion, a proximal end portion, and a central lumen extending therethrough between a distal opening and a proximal opening. The central lumen defines a proximal portion and a distal portion and is configured to receive a portion of a pin within the distal portion thereof. The insertion tool including a retention channel defined about the housing at the distal end portion thereof. The retention channel is disposed in communication with the distal portion of the central lumen. A D-ring is at least partially seated within the retention channel and extends into the distal portion of the central lumen to retain the pin therein by applying a compressive force to the pin. A plunger is configured to slide through the central lumen to deploy the pin distally from the distal opening of the central lumen.

In an aspect, the retention channel defines a D-shape such that the D-ring conforms to the D-shape. The D-ring may define any suitable at-rest shape, e.g., before engagement within the D-shape retention channel such as, for example, an O-ring shape.

In another aspect, the central lumen defines a first and a second diameter. The first diameter is disposed at the distal portion of the central lumen and approximates a diameter of the pin and the second diameter is disposed at the proximal portion of the central lumen and approximates a diameter of the plunger. In such aspects, a stop portion may be defined between the proximal portion of the central lumen and the distal portion of the central lumen to limit distal advancement of the plunger.

In still another aspect, a spring may be disposed within the central lumen of the housing. The spring may be a compression spring.

In still yet another aspect, a drive shaft extends distally from the plunger. The drive shaft is configured to contact the pin and deploy the pin from the housing.

In another aspect, the distal end portion of the housing has a substantially D-shaped portion. The D-shaped portion of the housing may be disposed between the distal opening of the central lumen and the retention channel.

In another aspect, the housing further has at least one elongated opening configured to receive a dowel engaged with the plunger to inhibit relative rotation between the plunger and the housing.

In yet another aspect, the dowel is configured to slide along the at least one elongated opening as the plunger slides through the housing.

In still another aspect, the elongated opening defines a length proportional to a selected displacement of the plunger relative to the housing from an un-actuated position to an actuated position.

The present disclosure also provides a method of assembling a portion of a surgical instrument including positioning at least one component of a surgical instrument for receipt of a pin through an aperture. The method further includes engaging the pin partially within a central lumen of an insertion tool, where a D-ring of the insertion tool applies a compressive force to retain the pin in engagement partially within the central lumen. The method further includes aligning the pivot pin with the aperture of the at least one component and actuating a plunger of the insertion tool through the central lumen to deploy the pivot pin distally from the central lumen and into the aperture.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Various aspects and features of the present disclosure described herein with reference to the drawings wherein.

DETAILED DESCRIPTION

Figure 1A:
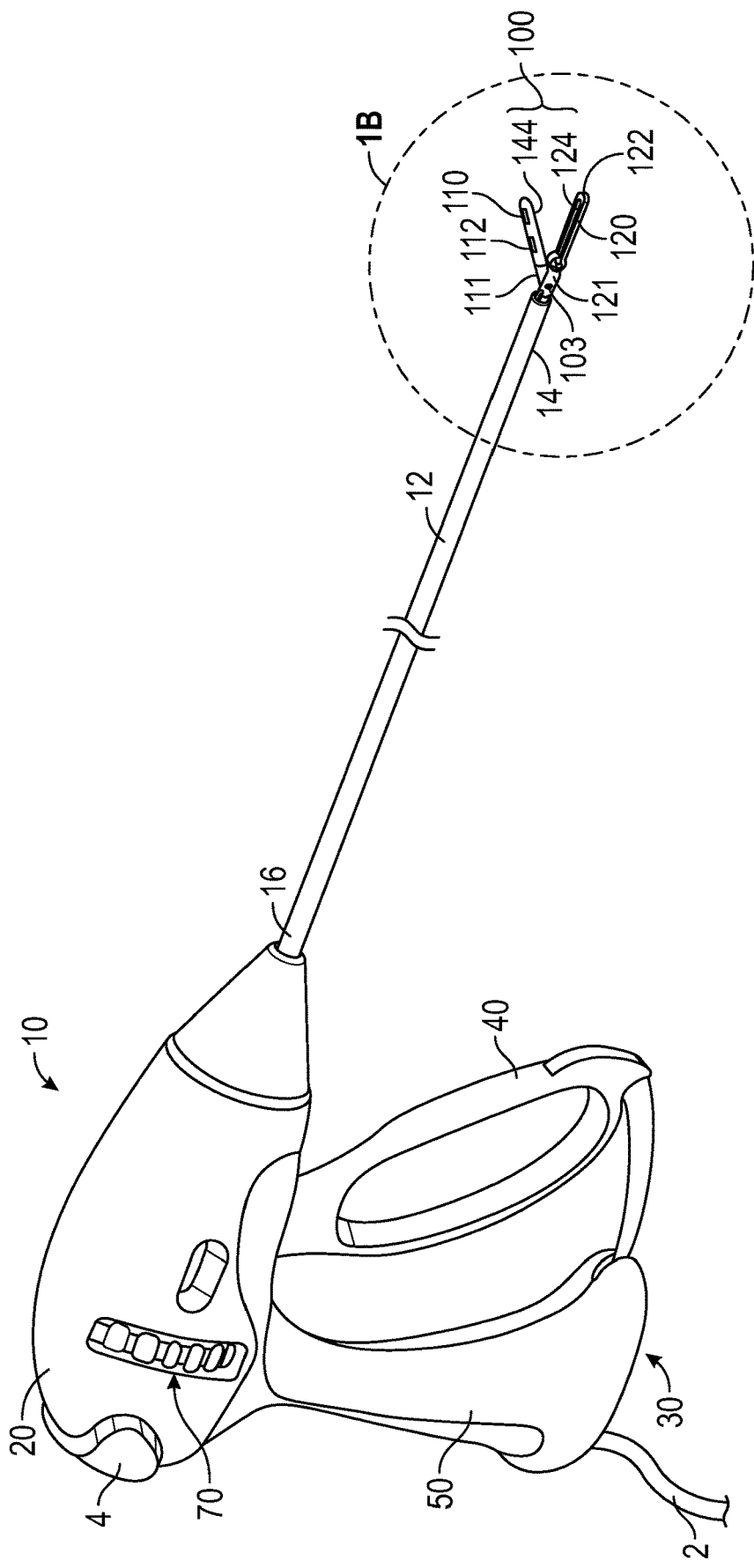
FIG. 1A is a perspective view of a shaft-based surgical forceps.
Figure 2:
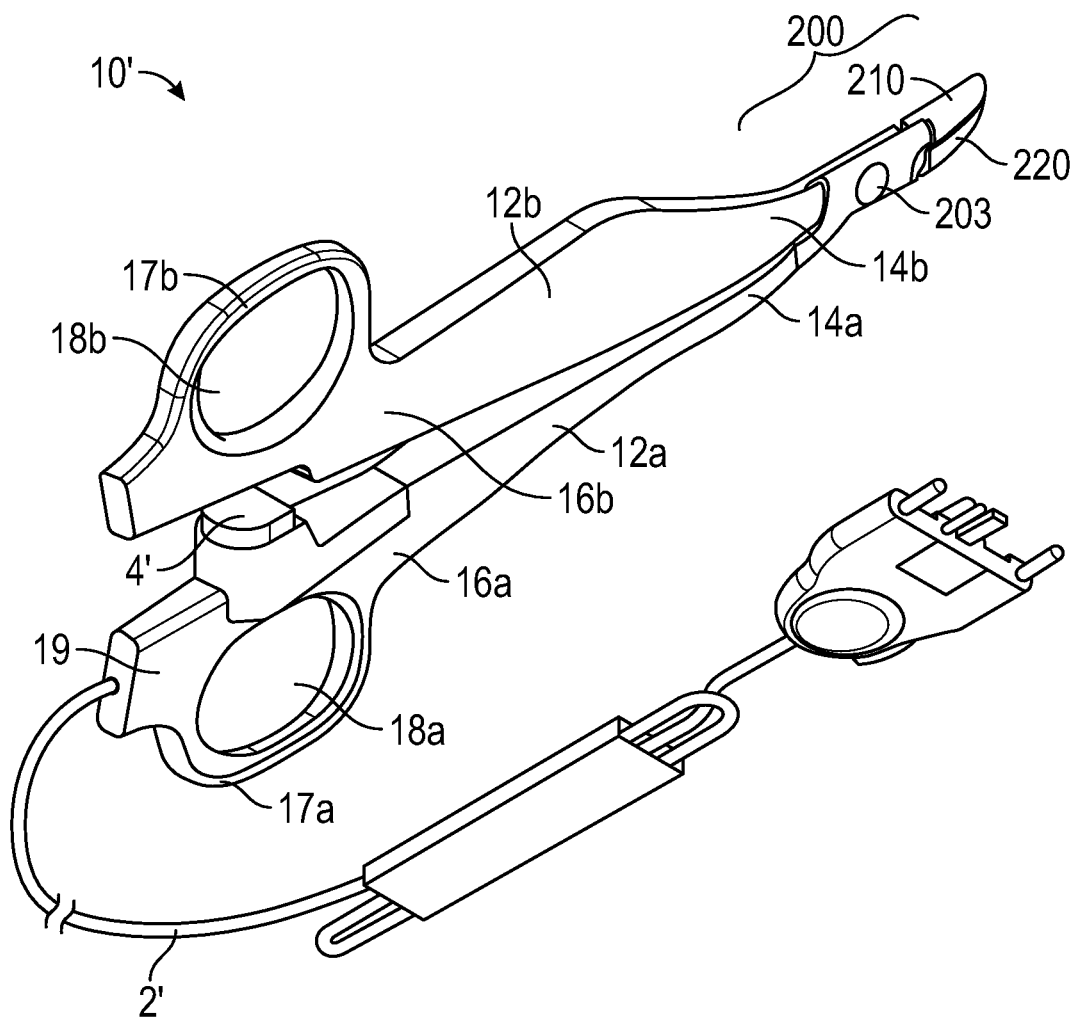
FIG. 2 is a perspective view of a hemostat-style surgical forceps.

Turning to FIGS. 1A and 2, FIG. 1A depicts a shaft-based surgical forceps 10 and FIG. 2 depicts a hemostat-style forceps 10'. The aspects and features of the present disclosure are applicable to forceps 10, forceps 10', or any other suitable surgical instrument. Obviously, different electrical and mechanical connections and considerations apply to each particular type of instrument; however, the aspects and features of the present disclosure remain generally consistent regardless of the particular instrument used.

Figure 1B:
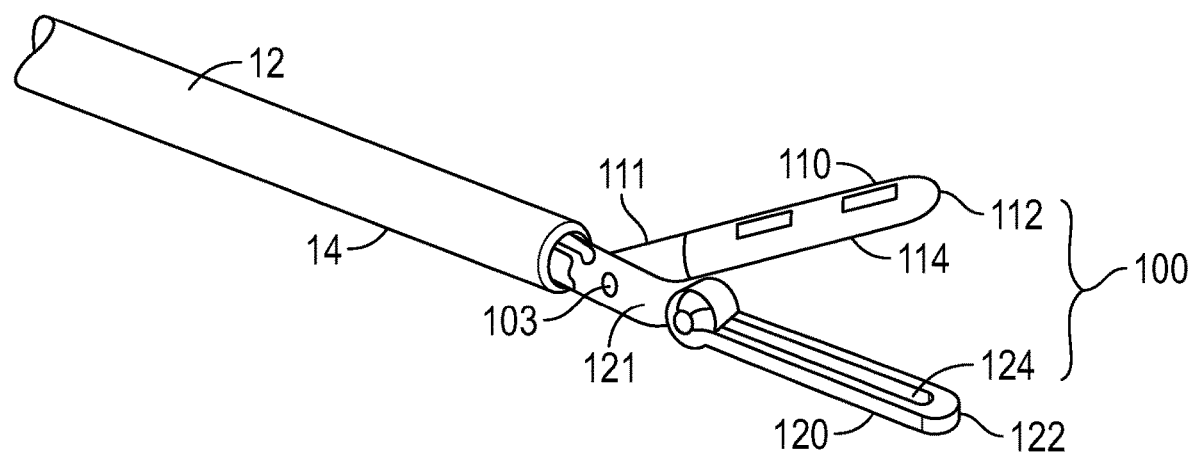
FIG. 1B is an enlarged, perspective view of the area of detail indicated as "1B" in FIG. 1A, illustrating an end effector assembly of the forceps of FIG. 1A.

Referring to FIGS. 1A and 1B, forceps 10 generally includes a housing 20, a handle assembly 30, a rotating assembly 70, an activation switch 4, and an end effector assembly 100. Forceps 10 further includes a shaft 12 having a distal end 14 configured to mechanically engage end effector assembly 100 and a proximal end 16 that mechanically engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating surfaces 114, 124 of jaw members 110, 120, respectively. However, energy may be supplied to respective tissue-treating surfaces 114, 124 of jaw members 110, 120 in any other suitable fashion, e.g., via conductive structural components of forceps 10, brush-contacts, etc. Activation switch 4 is electrically coupled with the supply of energy to enable the selective supply of energy to tissue-treating surfaces 114, 124 of jaw members 110, 120, respectively, for treating tissue grasped therebetween. Rotating assembly 70 is rotatable in either direction to rotate end effector assembly 100 relative to housing 20.

Handle assembly 30 includes a fixed handle 50 and a movable handle 40. Fixed handle 50 is integrally associated with housing 20 and movable handle 40 is movable relative to fixed handle 50. More specifically, movable handle 40 is pivotably coupled to housing 20 within housing 20 via a pivot pin (not shown) and operably coupled to a drive assembly (not shown) disposed within housing 20 such that movable handle 40 and the drive assembly (not shown), together, mechanically cooperate to impart movement of one or both jaw members 110, 120 about a pivot pin 103 between a spaced-apart position and an approximated position to grasp tissue between jaw members 110, 120. As shown in FIG. 1A, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120.

Referring to FIG. 2, forceps 10' is shown including two elongated shaft members 12a, 12b, each having a proximal end 16a, 16b, and a distal end 14a, 14b, respectively. Forceps 10' further includes an end effector assembly 200 similar to end effector assembly 100 (FIGS. 1A and 1B). More specifically, end effector assembly 200 includes first and second jaw members 210, 220 attached to respective distal ends 14a, 14b of shaft members 12a, 12b and pivotably coupled to one another about a pivot pin 203. Each shaft member 12a, 12b includes a handle 17a, 17b disposed at the proximal end 16a, 16b thereof. Each handle 17a, 17b defines a finger hole 18a, 18b therethrough for receiving a user's finger. As shown, finger holes 18a, 18b facilitate movement of the shaft members 12a, 12b relative to one another to, in turn, pivot jaw members 210, 220 between a spaced-apart position and an approximated position for grasping tissue therebetween.

One of the shaft members 12a, 12b of forceps 10', e.g., shaft member 12a, includes a proximal shaft connector 19 configured to connect the forceps 10' to a source of energy (not shown), e.g., a generator. Proximal shaft connector 19 secures a cable 2' to forceps 10' such that the user may selectively supply energy to jaw members 210, 220 for treating tissue grasped therebetween. More specifically, an activation switch 4' is positioned to initiate the supply of energy to jaw members 210, 220 upon sufficient approximation of shaft members 12a, 12b.

With reference to FIG. 1B, end effector assembly 100 of forceps 10 (FIG. 1A) is shown, keeping in mind that end effector assembly 200 (FIG. 1A) includes similar features. Each jaw member 110, 120 of end effector assembly 100 includes a proximal flange 111, 121 and a distal jaw body 112, 122 upon which respective tissue-treating surfaces 114, 124 are defined. Proximal flanges 111, 121 are pivotably coupled to one another about the pivot pin 103. One or both of proximal flanges 111, 121 is pivotably coupled to shaft 12 via pivot pin 103 and operably coupled to the drive assembly (not shown) such that movable handle 40 (FIG. 1A) is operable to pivot jaw members 110, 120 relative to one another between the spaced-apart and approximated positions.

Now with reference to FIGS. 3A-8, a pin insertion tool 300 utilized to facilitate the assembly of a surgical instrument such as forceps 10 (FIG. 1A), forceps 10' (FIG. 2), or any other suitable surgical instrument is shown. The pin insertion tool 300 is configured for use in installing a pin such as the pivot pin 103 of end effector assembly 100 (see FIG. 1B) to coupled portions of a surgical device, for example, pivotably coupling jaw member 110 with jaw member 120 and shaft 12 of forceps 10 (see FIGS. 1A and 1B). The pin insertion tool 300 may alternatively or additionally be configured for use in installing any other pin, e.g., pivot pin, cam pin, retention pin, etc., associated with any suitable surgical instrument or component thereof.

Referring to FIG. 3A-5, the pin insertion tool 300 includes a housing 310, a plunger 320, a drive shaft 330, a spring 340, a dowel 350, and a D-ring 360. The pin insertion tool 300 is generally configured to manipulate a pin, e.g., pivot pin 103 or pivot pin 203 (FIG. 2). Specifically, the housing 310 is configured to be grasped by a user along with the plunger 320, which is manipulatable to position and insert a pin such as the pivot pin 103. The pin insertion tool 300 or a portion thereof is configured to receive the pivot pin 103, retain the pivot pin 103, and ultimately deliver the pivot pin 103 into a selected portion of a surgical instrument such as forceps 10 (FIG. 1A) or forceps 10' (FIG. 2). The housing 310 of the pin insertion tool 300 is configured to operably receive the plunger 320, the drive shaft 330, and the pivot pin 103, as detailed below. The pivot pin 103 is releasably retained partially within the housing 310 by the D-ring 360. With the pivot pin 103 retained partially within the housing 310, the plunger 320 is actuated, e.g., driven into the housing 310, and, as a result, the drive shaft 330 (which is connected to and extends distally from the plunger 320) deploys the pivot pin 103 distally from the housing 310. Moreover, the spring 340 biases the plunger 320 proximally, e.g., away from the housing 310 and the actuated position, and thus serves to retract the plunger 320 to its initial position after actuation and release, e.g., after the pivot pin 103 is deployed from the housing 310 and plunger 320 is released. The pin insertion tool 300 and methods of use thereof are described more in detail below. In embodiments, the pin insertion tool 300 may further include a plunger handle 333 configured to aid in the manipulation of the plunger 320 and/or pin insertion tool 300 as a whole.

Figure 3A:
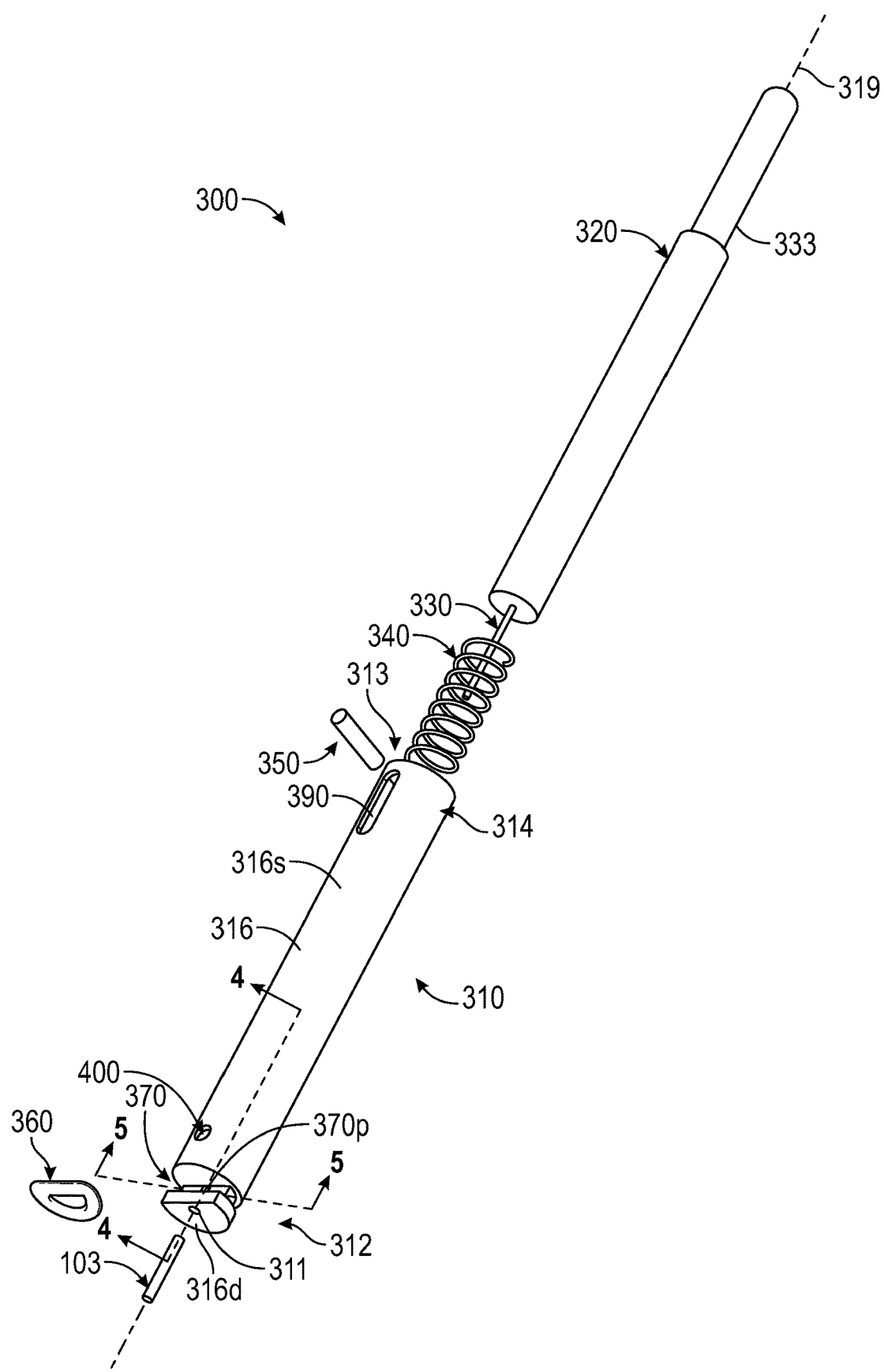
FIG. 3A is a first, exploded, perspective view of an insertion tool provided in accordance with the present disclosure and configured to facilitate assembly of the end effector assembly of the forceps of FIG. 1A or of any other suitable assembly.
Figure 3B:
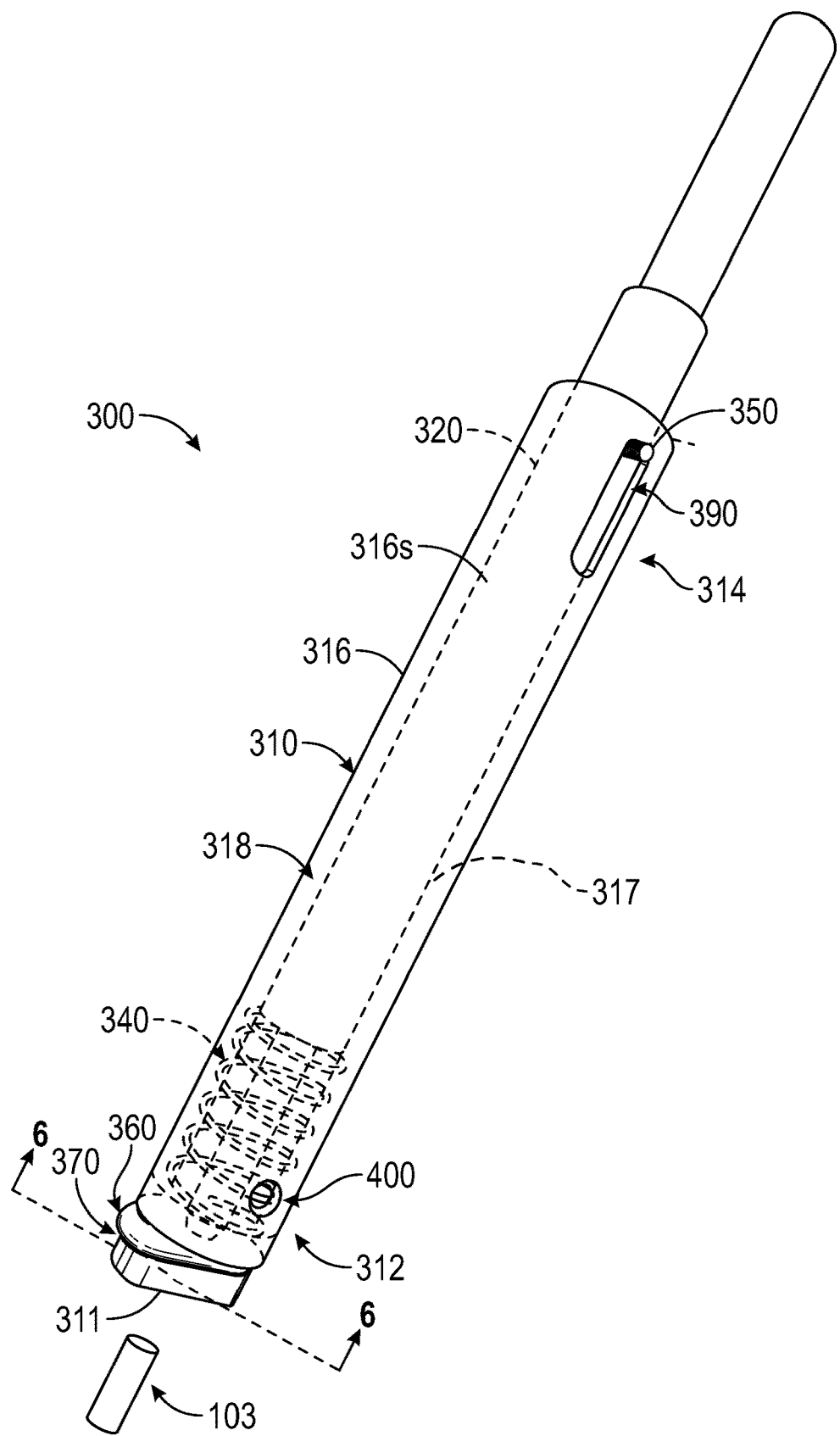
FIG. 3B is a perspective view of the insertion tool of FIG. 3A prior to connecting a pivot pin therewith.
Figure 3C:
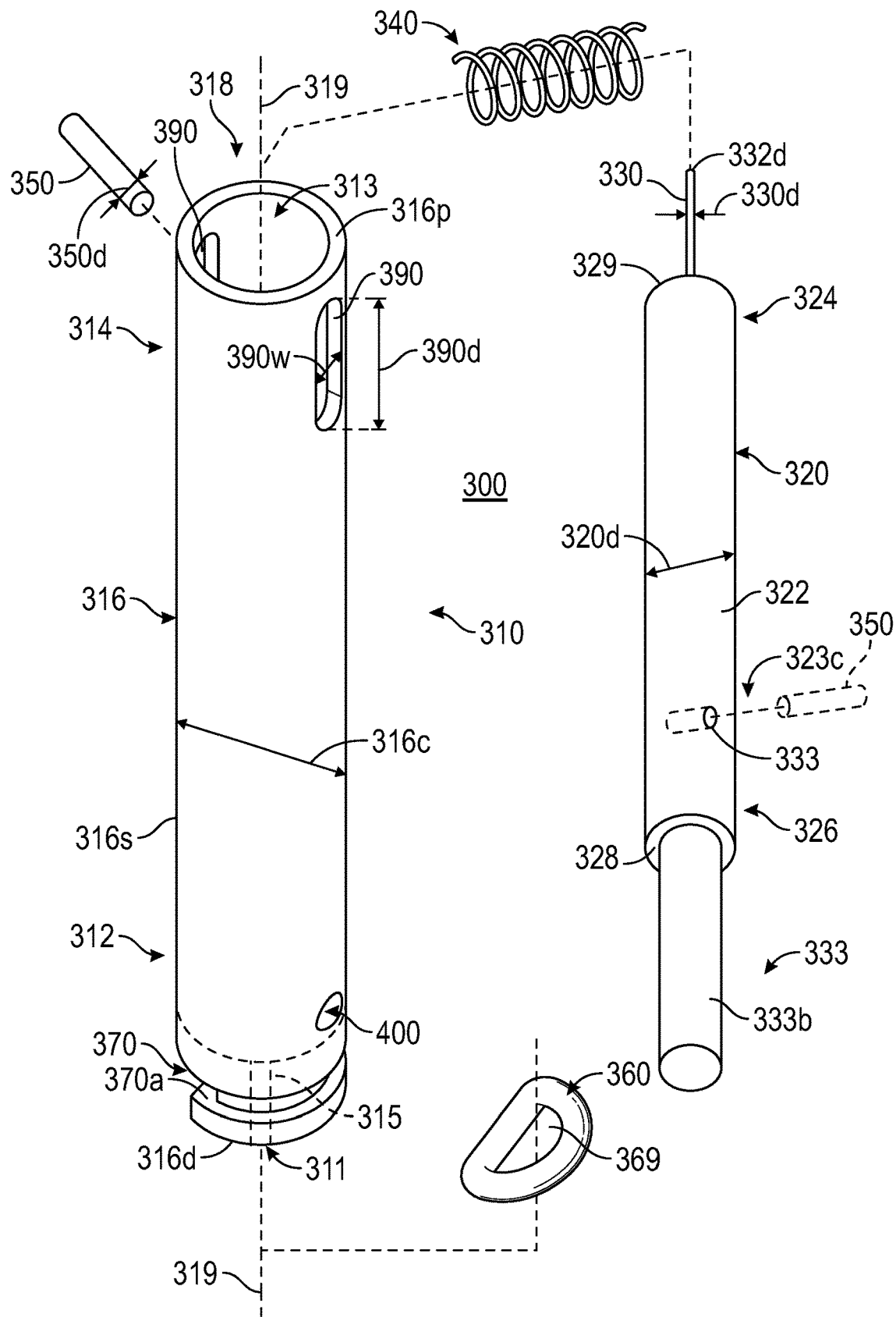
FIG. 3C is a second, exploded, perspective view of the insertion tool of FIG. 3A.

With reference to FIGS. 3A-3C, the housing 310 of the pin insertion tool 300 defines a tubular, rectangular or other suitable configuration. As best seen in FIGS. 3A and 3B, the housing 310 includes a housing distal end portion 312, a housing proximal end portion 314, a housing body 316 extending between the proximal and distal end portions 314, 312, respectively, and a central lumen 318. Additionally, the housing 310 includes a annular retention channel 370, at least one oblong slot 390, and at least one inspection hole 400. The housing body 316 includes a tubular outer surface 316s, a distal surface 316d, a proximal surface 316p (FIG. 3C), and a defines a housing body diameter 316c. The tubular outer surface 316s of the housing 310 extends between the distal surface 316d and the proximal surface 316p. The distal surface 316d and the proximal surface 316p of the housing 310 may be substantially flat.

The central lumen 318 of the housing 310 is configured to extend through the housing body 316 and defines a central axis 319, a distal opening 311 (FIG. 3A), and a proximal opening 313. The distal opening 311 is smaller in diameter than the proximal opening 313. However, in embodiments, the distal opening 311 and the proximal opening 313 may be equal in diameter or the proximal opening 313 may be larger. Further, the central lumen 318 can be configured as a stepped channel including a narrow pin retention portion 315 (FIG. 3C) connected to and in communication with a wide plunger track portion 317 (FIG. 3B). The narrow pin retention portion 315 is configured to receive and retain a portion of the pivot pin 103 and to slidably receive the drive shaft 330 to deploy the pivot pin 103. The wide plunger track portion 317 is configured to slidably receive the plunger 320 and the drive shaft 330. The narrow pin retention portion 315 is connected to the distal opening 311. As shown (FIG. 4), the two 315, 311 are similar in diameter, e.g., within 10%. However, in embodiments, the narrow pin retention portion 315 and the connected distal opening 311 may not be equal in diameter. Further, the narrow pin retention portion 315 and the drive shaft 330 may have substantially similar diameters, e.g., within 10%. The wide plunger track portion 317 or a portion thereof and the plunger 320 or a portion thereof may have substantially similar diameters, e.g., within 10%, or may have different diameters.

Figure 4:
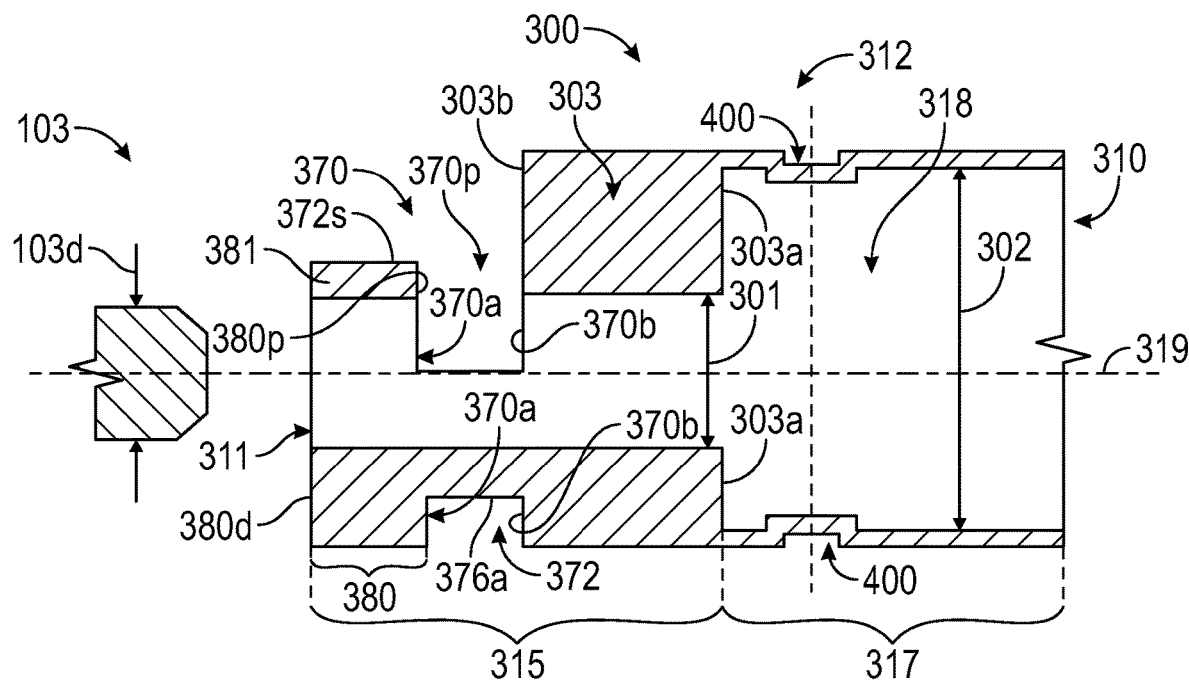
FIG. 4 is an enlarged, longitudinal cross-sectional view of the insertion tool of FIG. 3A taken across section line "4-4" in FIG. 3A.

Turning now to FIG. 4, the central lumen 318 includes a first diameter 301, a second diameter 302, and a stopping portion 303 (a portion of the housing 310 may define the stopping portion 303). The first diameter 301 is defined in the narrow pin retention portion 315. A pivot pin diameter 103d of the pivot pin 103 and/or a drive shaft diameter 330d of the drive shaft 330 (FIG. 3C) may be substantially similar to the first diameter 301. The second diameter 302 is defined in the wide plunger track portion 317 and in embodiments may be substantially equal (e.g., within 10%) to a diameter 320d of the plunger 320. The stopping portion 303 is disposed between the annular retention channel 370 and the housing 310 and the wide plunger track portion 317 of the central lumen 318. The stopping portion 303 connects the annular retention channel 370 with the wide plunger track portion 317. The stopping portion 303 of the central lumen 318 includes a stopping surface 303a and a retention channel surface 303b that opposes the stopping surface 303a. The retention channel surface 303b engages the D-ring 360. The stopping surface 303a can limit the advancement of the plunger 320. In embodiments, the stopping surface 303a may engage the distal end of the spring 340.

Figure 5:
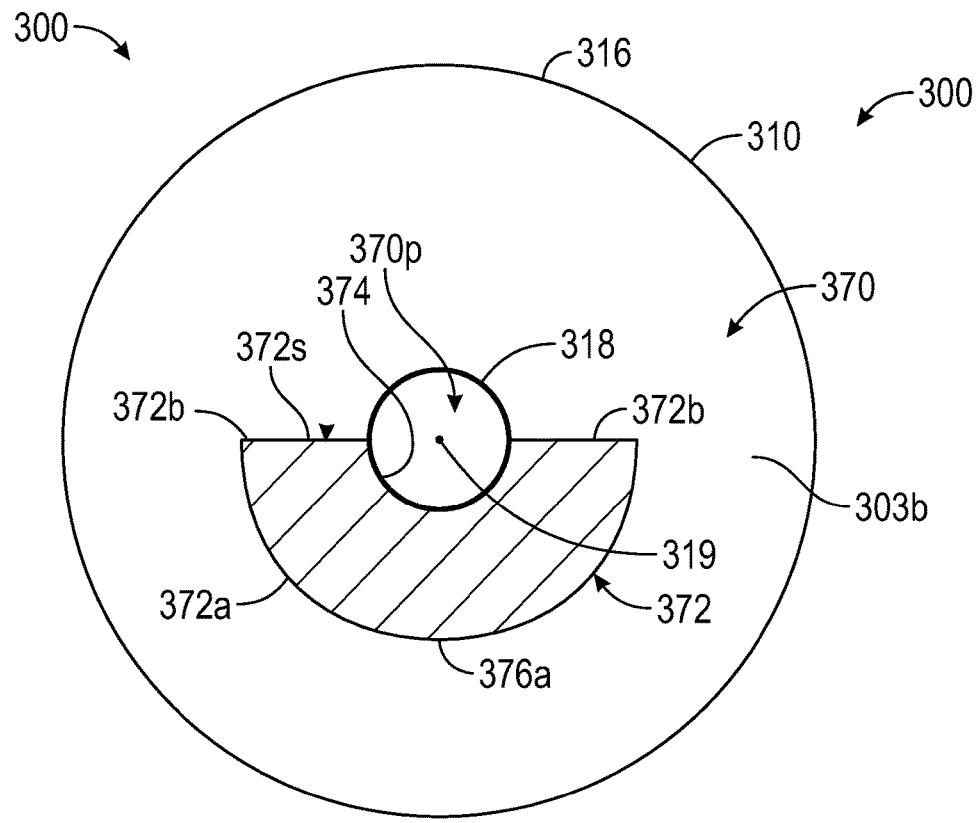
FIG. 5 is an enlarged, transverse, cross-sectional view of the insertion tool of FIG. 3A taken across section line "5-5" in FIG. 3A.

Still referring to FIG. 4 and, in addition, to FIG. 5, the annular retention channel 370 is disposed at the distal end portion 312 of the housing 310 and is configured to host the D-ring 360 (at least partially therein). The annular retention channel 370 may be defined as a recess extending continuously or discontinuously around the distal end portion 312 of the housing 310. The annular retention channel 370 is defined by a distal channel surface 370a, a proximal channel surface 370b, and a central core 372. The distal channel surface 370a and the proximal channel surface 370b may have as similar radii; however, in embodiments, the two channel surfaces 370a, 370b may have different radii. The proximal channel surface 370b may coincide with the proximal channel surface 303b. The distal channel surface 370a may define a half ring-like cross-sectional shape (FIG. 5) such that the distal channel surface 370a defines a D-shaped configuration.

The central core 372 defining the annular retention channel 370 is disposed between the proximal channel surface 370b and the distal channel surface 370a (FIG. 4), connecting the two channel surfaces 370a, 370b, and may define a D-shaped configuration wherein the flat portion thereof is aligned on the central axis 319. As shown, the central core 372 is a half circle including a half circle-circular recession forming a half pipe recess 374 (FIG. 5). Specifically, the central core 372 includes a semi-tubular portion 372a, two flat portions 372b, and the half pipe recess 374. The semi-tubular portion 372a defines a tubular surface 376a. Each of the two flat portions 372b defines a surface 372s (FIGS. 4 and 5). The two flat portions 372b define a channel opening 370p communicating with the central lumen 318 and the half pipe recess 374 of the annular retention channel 370. The channel opening 370p may include a rectangular configuration (see FIG. 3A) defined between the two flat portions 372b and the two channel surface 370a, 370b, and above the half pipe recess 374.

Figure 6:
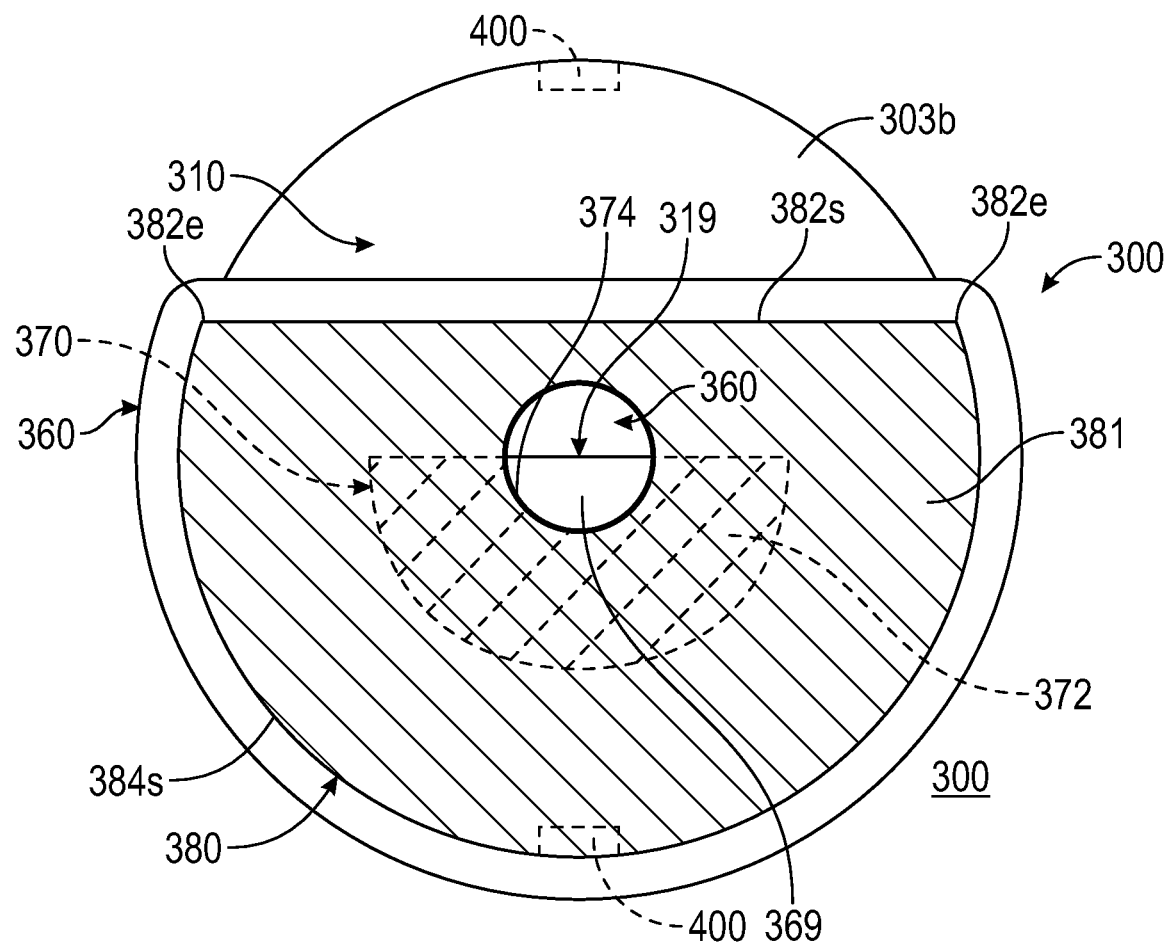
FIG. 6 is an enlarged, transverse, cross-sectional view of the insertion tool of FIG. 3A taken across section line "6-6" in FIG. 3B.

Still with reference to FIG. 4 and in addition to FIG. 6, the pin insertion tool 300 includes a distal tip 380 (FIG. 4) configured to aid with retention of the D-ring 360 within the annular retention channel 370. Specifically, distal tip 380 extends distally from the central core 372 and encompasses a portion of the narrow pin retention portion 315 of the central lumen 318. Distal tip 380 can be formed as a portion of the housing 310 distally of the annular retention channel 370, e.g., between the distal channel surface 370a and the distal opening 311 or may be formed separately therefrom and subsequently attached thereto in a similar position. The distal tip 380 includes a distal tip body 381, a distal surface 380d (FIG. 4) and a proximal surface 380p (FIG. 4). As shown, the proximal surface 380p is coincident with the distal channel surface 370a and the distal surface 380d is a portion of the distal surface 316d (FIG. 3A) of the housing 310. As shown, surfaces 380d and 316d are coincident. Further, the distal tip body 381 of the distal tip 380 can include a cross-sectional D-shaped configuration (FIG. 5). A flat distal tip portion is defined by a flat surface 382s extending between two edges 382e and is disposed adjacent to the narrow pin retention portion 315 of the central lumen 318. A semi-tubular distal tip portion 384 is defined by a tubular surface 384s that meets the flat surface 382s at the two edges 382e. As shown in FIG. 6, the tubular surface 384s is an extension of the tubular outer surface 316s of the housing 310.

Turning back to FIGS. 3B and 3C, as noted above, the housing 310 of the pin insertion tool 300 can include at least one oblong slot 390 and at least one inspection hole 400. The at least one oblong slot 390 includes a length 390d and a width 390w (FIG. 3C). As shown, the pin insertion tool 300 includes two oblong slots 390 configured to align with one another on either side of the central lumen 318. The at least one inspection hole 400 may be defined through the housing 310 to enable inspection of the central lumen 318 and/or to release air trapped therein during actuation of the pin insertion tool 300. As shown, the pin insertion tool 300 includes two inspection holes 400 aligned with one another on either side of central lumen 318.

The width 390w of the at least one oblong slot 390 generally approximates (e.g., within 10% of) the diameter 350d of the dowel pin 350 (FIG. 3C). The length 390d of the at least one oblong slot 390 may correspond to a desired maximum displacement of the plunger 320. For example, the length 390d may generally approximate a selected distance of travel for the plunger 320 (and thus the drive shaft 330) along the wide plunger track portion 317 of the central lumen 318.

Figure 7A:
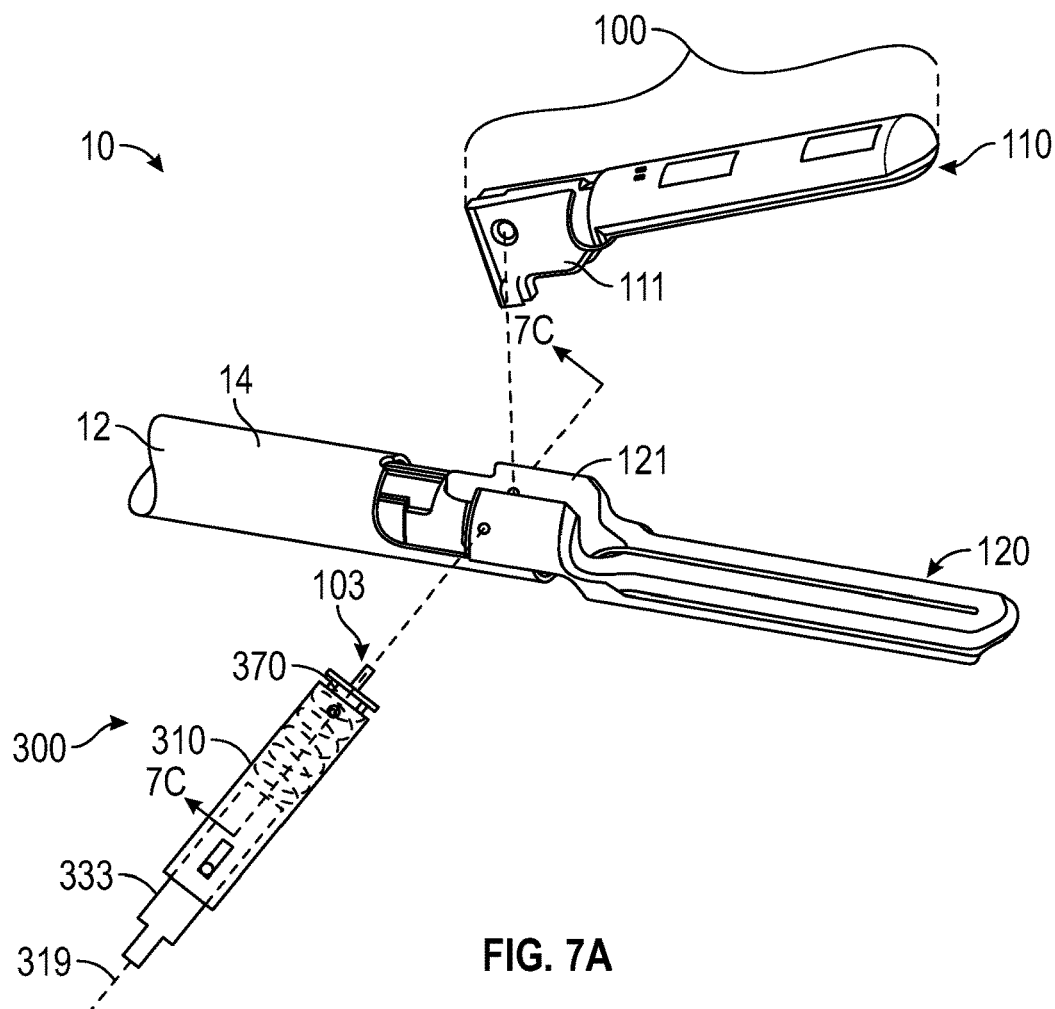
FIGS. 7A-7D depict an exemplary sequence illustrating assembly of the end effector assembly of FIG. 1A in accordance with aspects of the present disclosure, using the insertion tool of FIG. 3A.
Figure 7B:
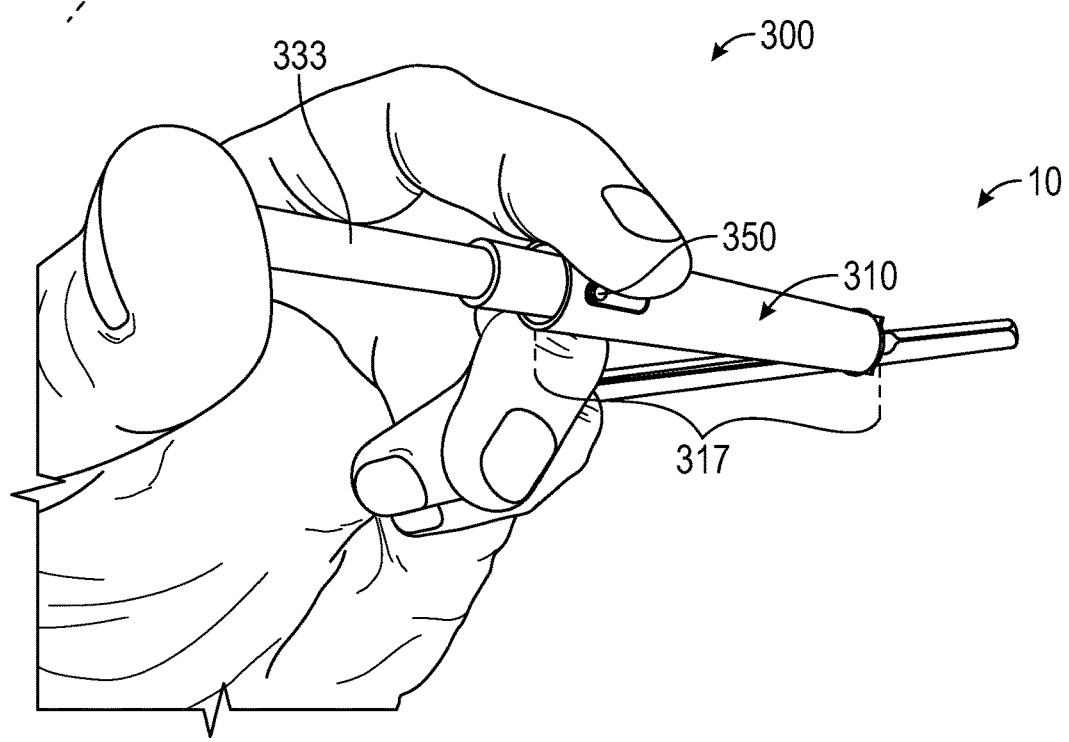
Figure 7C:
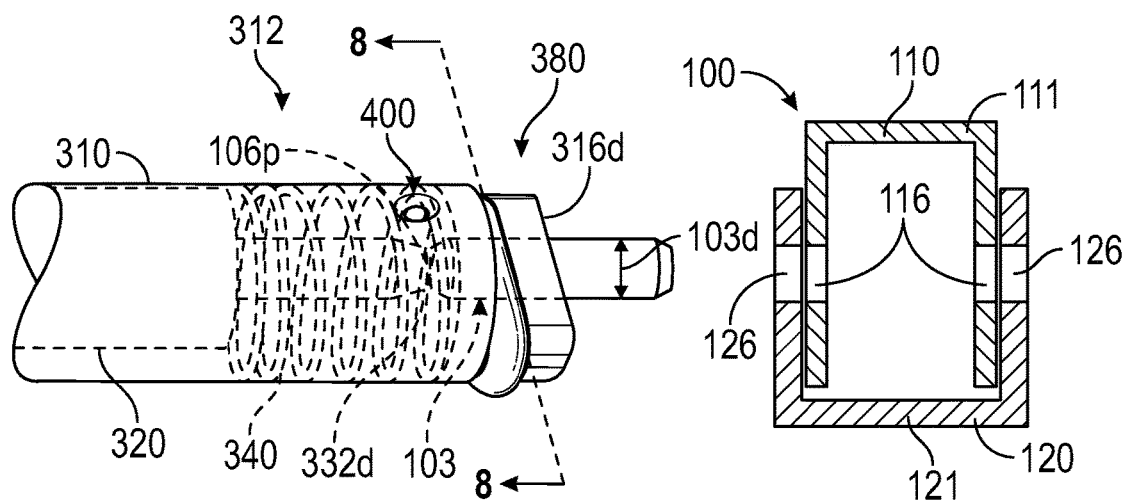
Figure 7D:
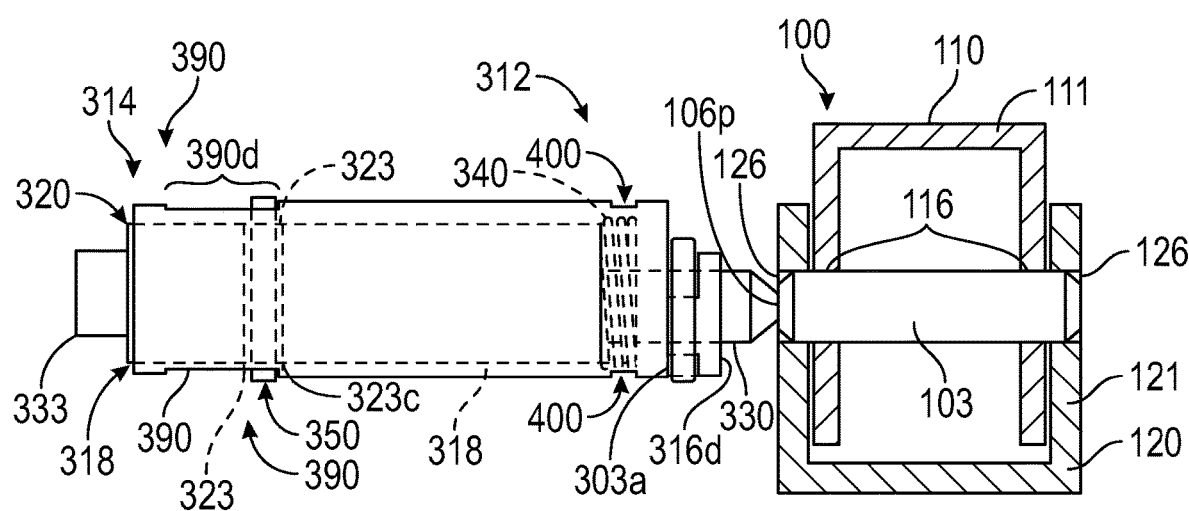

Still with reference to FIG. 3C, the plunger 320 includes a plunger body 322, a plunger distal end portion 324, a plunger proximal end portion 326, a plunger distal surface 328, a plunger proximal surface 329, at least one opening 323, and a channel 323c (FIGS. 3C and 7D). The plunger body 322 extends between the proximal and distal end portions 324, 326, respectively, and defines the plunger diameter 320d. The plunger body 322 is cylindrical; however, the plunger body 322 can be rectangular, triangular, or other shape. The at least one opening 323 is connected to the channel 323c and extends perpendicularly to a longitudinal axis of the plunger body 322. The channel 323c is configured to receive the dowel 350 therein and can extend partially or fully through the plunger body 322. The plunger 320 is configured to fixedly engage the drive shaft 330 and the plunger handle 333. Alternatively, the plunger 320 can be monolithically formed along with the drive shaft 330 and/or the plunger handle 333.

The dowel 350 is slidably received through the at least one oblong slot 390 such that a range of motion of the plunger 320 is defined via movement of the dowel 350 through at least one oblong slot 390. However, in embodiments, other configurations to define the range of motion of the plunger 320 may be utilized, e.g., such as track paired with a central lumen 318, a cap retaining the plunger 320 within the central lumen 318, etc.

As shown in FIG. 3C, the drive shaft 330 includes a distal surface 332d and a proximal surface (not shown). As shown, the drive shaft 330 and the plunger 320 are monolithically formed with the drive shaft 330 extending distally from the plunger distal surface 328. The drive shaft 330 can be configured to pass through the narrow pin retention portion 315 and out distal opening 311 of the housing 310 (see FIG. 4). The drive shaft diameter 330d can be smaller than the plunger diameter 320d, however, in selected configurations the plunger diameter 320d and the drive shaft diameter 320d may be substantially similar.

Still referring to FIG. 3C, the pin insertion tool 300 may further include a resilient member associated with the housing 310 and the plunger 320, such as the spring 340, a foam, or other suitable resilient member. As shown in FIG. 3B, the spring 340 is disposed within the housing 310, between the stopping surface 303a (FIG. 4) of the housing 310 and the distal surface 328 of the plunger 320, and about the drive shaft 330. The spring 340 may be a coil compression spring or other suitable spring.

Figure 8:
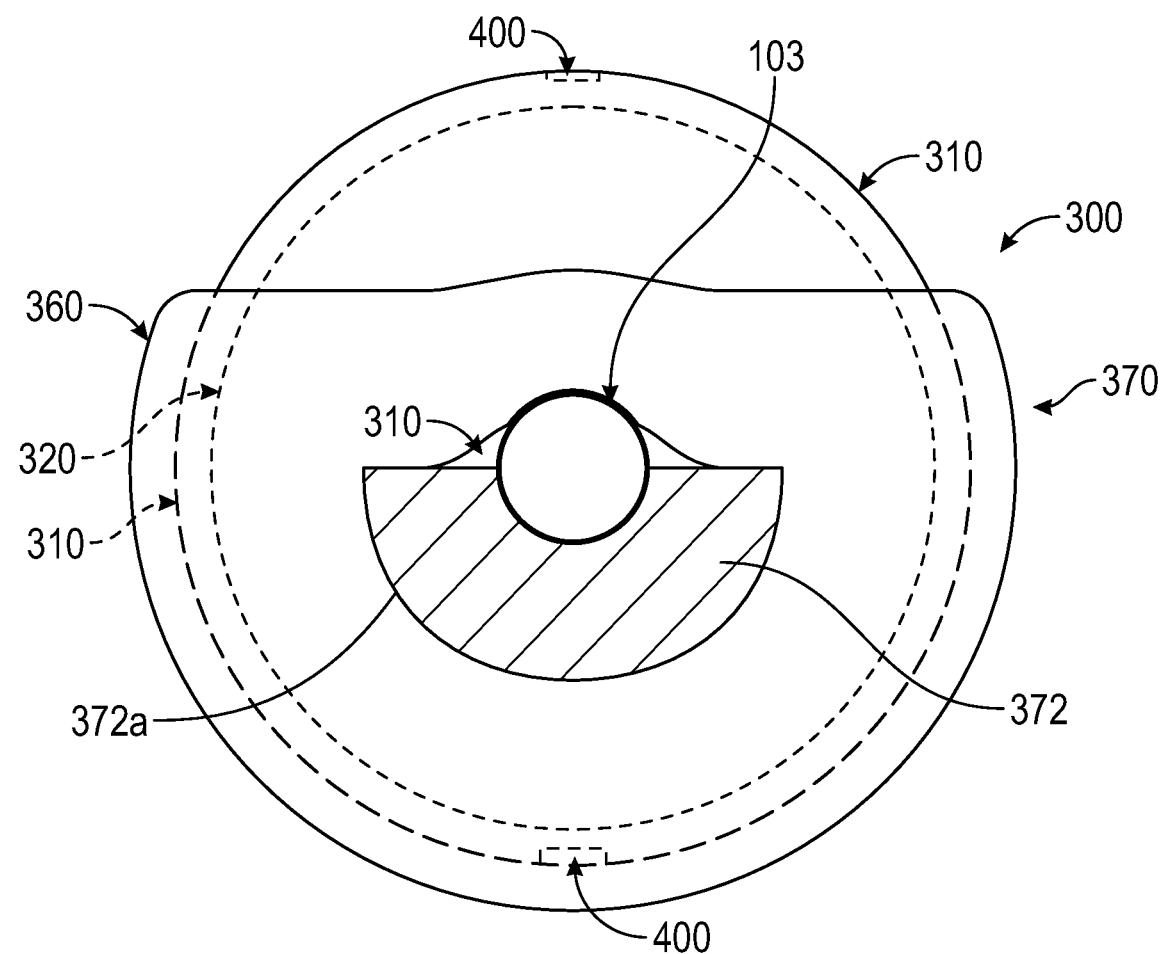
FIG. 8 is an enlarged, transverse cross-sectional view of the insertion tool of FIG. 3A taken across section line "8-8" in FIG. 7C.

Moving forward to FIGS. 6 and 8, the insertion tool 300 further includes the D-ring 360 or other suitable elastomeric member. The D-ring 360 is seated in the annular retention channel 370 and under tension and extends into the half pipe recess 374 such that when the pivot pin 103 is disposed therein, a portion of the D-ring 360 presses against the pivot pin 103 to retain the pivot pin 103 therein under compression. The D-ring 360 assumes a D-shape when engaged within the annular retention channel 370 but may be configured to define any suitable at-rest shape, e.g., an O-ring shape. As shown in FIG. 3C, the D-ring 360 includes an opening 369. The D-ring 360 and the annular retention channel 370 may be substantially similar in shape and configured as mating-elements or may define other configurations.

Now with reference to FIGS. 7A-8, the use of pin insertion tool 300 for facilitating the assembly of forceps 10 (FIG. 1A), e.g., the pivotable coupling of jaw member 110 with jaw member 120 and shaft 12 (FIG. 1A) is detailed. Initially, with reference to FIG. 7A, proximal flanges 111, 121 of jaw members 110, 120, respectively, are aligned with one another such that the pairs of apertures 116, 126 (see FIGS. 7C and 7D) defined through respective proximal flanges 111, 121 are aligned with one another.

With reference to FIGS. 7C and 8, retention of a pivot pit such the pivot pin 103 (or pivot pin 203) into the pin insertion tool 300 is detailed. The pivot pin 103 is inserted through the distal opening 311 of housing 310 and is urged through the aperture 369 of the D-ring 360, expanding the D-ring 360 to pass therethrough. As such, the bias of the D-ring 360 inwardly applies a compressive force to retain the pivot pin 103 within the distal end portion 312 of the housing 310 (see FIG. 8) and against the half pipe recess 374 of the annular retention channel 370. In this inserted position, a portion of the pivot pin 103 extends distally from the housing 310.

After the pivot pin 103 is retained within the pin insertion tool 300 via the D-ring 360 and the housing 310, the pin insertion tool 300 is positioned with the pivot pin 103 (now loaded within the pin insertion tool 300) aligned with the pairs of apertures 116, 126 (FIG. 7C). Thereafter, the plunger 320 is actuated by pushing the plunger handle 333 distally relative to the housing 310 and towards the forceps 10 to urge the plunger 320 through the central lumen 318 until engagement of the distal surface 332d of the drive shaft 330 with the proximal surface 106p of the pivot pin 103 (FIG. 7C). Ultimately, the user keeps pushing the plunger handle 333 in this manner until the drive shaft 330 urges the pivot pin 103 to deploy from the pin insertion tool 300 and through the aligned apertures 126, 116. Once the pivot pin 103 is inserted through each set of aligned apertures 116, 126 sufficiently so as to pivotably couple proximal flanges 111, 121 to one another (FIG. 7C), the pivot pin 103 may further be secured in position, e.g., via welding, mechanical capping, etc., to inhibit dislodging of the pivot pin 103 from apertures 116, 126, if necessary.

With reference to FIG. 7D, during the above-detailed use, the dowel 350 rides in the at least one oblong slot 390 of the housing 310 to stop the plunger 320 from over-actuation. Additionally, the receipt of the dowel 350 within the at least one oblong slot 390 substantially reduces or stops rotational movement of the plunger 320 when ridding the central lumen 318. The spring 340, compressed during actuation, returns the plunger 320 to the initial position after actuation and release such that the pin insertion tool 300 is ready to be used to engage and install another pin.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

Additionally, It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). Moreover, while certain aspects of this disclosure are described as being performed by a single module or unit for purposes of clarity, it should be understood that the techniques of this disclosure may be performed by a combination of units or modules associated with, for example, a medical device.

What is claimed is:

1. An insertion tool facilitating assembly of a surgical instrument, comprising:
    a housing defining a distal end portion, a proximal end portion, and a central lumen extending therethrough between a distal opening and a proximal opening, wherein the central lumen defines a proximal portion and a distal portion, the central lumen configured to receive a portion of a pin within the distal portion thereof;
    a retention channel defined about the housing at the distal end portion thereof, the retention channel in communication with the distal portion of the central lumen;
    a D-ring at least partially seated within the retention channel and extending into the distal portion of the central lumen to retain the pin therein by applying a compressive force to the pin; and
    a plunger configured to slide through the central lumen to deploy the pin distally from the distal opening of the central lumen.

2. The insertion tool according to claim 1, wherein the retention channel defines a D-shape such that the D-ring conforms to the D-shape.

3. The insertion tool according to claim 1, wherein the central lumen defines a first and a second diameter, the first diameter is disposed at the distal portion of the central lumen and approximates a diameter of the pin and the second diameter is disposed at the proximal portion of the central lumen and approximates a diameter of the plunger.

4. The insertion tool according to claim 1, wherein a stop portion is defined between the proximal portion of the central lumen and the distal portion of the central lumen to limit distal advancement of the plunger.

5. The insertion tool according to claim 1, further including a spring disposed within the central lumen of the housing and configured to bias the plunger proximally.

6. The insertion tool according to claim 5, wherein the spring is a compression spring.

7. The insertion tool according to claim 5, further comprising a drive shaft extending distally from the plunger, the drive shaft configured to contact the pin and deploy the pin from the housing.

8. The insertion tool according to claim 1, wherein the distal end portion of the housing includes a substantially D-shaped portion.

9. The insertion tool according to claim 8, wherein the substantially D-shaped portion is disposed between the distal opening of the housing and the retention channel.

10. The insertion tool according to claim 1, wherein the housing further includes at least one elongated opening configured to receive a dowel engaged with the plunger to inhibit relative rotation between the plunger and the housing.

11. The insertion tool according to claim 10, wherein the dowel is configured to slide along the at least one elongated opening as the plunger slides through the central lumen.

12. The insertion tool according to claim 10, wherein the at least one elongated opening defines a length proportional to a selected displacement of the plunger relative to the housing from an un-actuated position to an actuated position.

13. A method of assembling a portion of a surgical instrument, comprising:
    positioning at least one component of the surgical instrument for receipt of a pin through an aperture of the surgical instrument;
    engaging the pin partially within a central lumen of an insertion tool, wherein a D-ring at least partially seated within a retention channel of the insertion tool applies a compressive force to retain the pin in engagement partially within the central lumen;
    aligning the pin with the aperture; and
    actuating a plunger of the insertion tool through the central lumen to deploy the pin distally from the central lumen and into the aperture.

* * * * *